United States Patent
Fabiano

(10) Patent No.: US 9,220,797 B2
(45) Date of Patent: Dec. 29, 2015

(54) METHOD AND APPARATUS FOR STERILIZING A LIQUID SOLUTION USING RADIO-FREQUENCY

(71) Applicant: Marco Fabiano, Calestano (IT)

(72) Inventor: Marco Fabiano, Calestano (IT)

(73) Assignee: G.E.A.F. S.R.L., Calestano (PR) (IT)

( * ) Notice: Subject to any disclaimer, the term of this patent is extended or adjusted under 35 U.S.C. 154(b) by 0 days.

(21) Appl. No.: 14/368,854

(22) PCT Filed: Dec. 10, 2012

(86) PCT No.: PCT/EP2012/074901
§ 371 (c)(1),
(2) Date: Jun. 26, 2014

(87) PCT Pub. No.: WO2013/098059
PCT Pub. Date: Jul. 4, 2013

(65) Prior Publication Data
US 2014/0363334 A1      Dec. 11, 2014

(30) Foreign Application Priority Data

Dec. 27, 2011 (IT) .............................. PR2011A0103

(51) Int. Cl.
| | |
|---|---|
| A61L 2/03 | (2006.01) |
| A61L 2/04 | (2006.01) |
| A61L 2/12 | (2006.01) |

(52) U.S. Cl.
CPC ... *A61L 2/03* (2013.01); *A61L 2/04* (2013.01); *A61L 2/12* (2013.01); *A61L 2202/23* (2013.01)

(58) Field of Classification Search
CPC .......................................................... A61L 2/03
USPC ............................................... 422/22, 186.21
See application file for complete search history.

(56) References Cited

U.S. PATENT DOCUMENTS

| | | |
|---|---|---|
| 5,476,634 A | 12/1995 | Bridges et al. |
| 2003/0205571 A1 | 11/2003 | Flugstad et al. |
| 2009/0304950 A1 | 12/2009 | Rostaing |

FOREIGN PATENT DOCUMENTS

WO      2008/107385 A1     9/2008

OTHER PUBLICATIONS

International Search Report, dated Jan. 16, 2013, from corresponding PCT application.

*Primary Examiner* — Sean E Conley
(74) *Attorney, Agent, or Firm* — Young & Thompson

(57) ABSTRACT

Process, and system, for sterilization of a product constituted by a non-distilled or demineralized liquid solution (3) contained in a rigid and/or flexible container (2). The process provides for at least one step of heating via capacitive supply of high-frequency current, with electrodes with facing surface of a closed-circuit electrode system (1) on the product, followed by a step of cooling with interruption of the supplied current; during at least part of the heating step, a counter-pressure pressure (P2) is supplied and acts inside the system (1) and on the product being treated.

10 Claims, 6 Drawing Sheets

METHOD AND APPARATUS FOR STERILIZING A LIQUID SOLUTION USING RADIO-FREQUENCY

FIELD OF APPLICATION OF THE INVENTION

It is an object of the present invention to provide a sterilization method and apparatus for liquids, in particular, liquids contained in rigid, such as glass, receptacles, or flexible, such as bags or tubular medical devices of polymeric plastic material.

STATE OF THE ART

Presently, sterilization of liquids, contained in rigid or flexible receptacles, for medical use, is achieved through heating in the range of 121° C., more generally between 120° C. and 125° C., and maintaining such temperature for a period of time determined as a function of coefficients depending on biological parameters.

The heating process is carried out, within autoclaves, by means of steam or overheated water which, contacting the external surfaces containers of infusion solutions, or other liquids for medical practice, heat the solutions themselves up to the desired temperature and for the time prescribed by various pharmacopeias.

Such heating, therefore, takes place from the outside towards the interior.

DISCLOSURE AND ADVANTAGES OF THE INVENTION

The aim of the present invention is to make available for the art a process, and related system, for sterilization of liquids in rigid and/or flexible containers, which provides generating a high-frequency electrical field between two half-shells shaped and acting as electrode and counter-electrode, and having internal surfaces matching the container The supplied power passes through the interior of the rigid or flexible container and reaches the non-demineralized liquid solution.

In other words, high frequency power is transferred to the one or more solutions to be sterilized by capacitive, low impedance means and, as a matter of fact, through the container itself, normally made of plastic insulating material or glass.

Heat is generated within the conductive liquid solution to be sterilized, and is convectively and conductively transferred towards the exterior. This means that the electrolytic solution under treatment becomes the conductive liquid mass in which heat is generated according to a ohmic type process and, hence, ohmic conduction: the liquid mass to be sterilized constitutes a dissipative conductor with homogeneous resistivity and/or conductivity.

ADVANTAGES

The above offers the following advantages:

Energy saving and limitation of dissipated power as it is associated to usage and method acting directly on the load (i.e. the container), without heating large external volumes, Possibility of direct insertion in production line, with bags and containers incoming from the filling line, A uniformly distributed heating above throughout the liquid mass to be sterilized, Rapid heating of the whole product, Negligible exterior-interior temperature gradient for container safeguard, Repeatability of the cycle, since an exact amount of power is deliverable in each cycle, Possibility of monitoring and measuring electrical parameters involved in the process; flexibility in terms of adjustment of supplied power and application times, Reduction of space usage.

Said objects and advantages are all achieved by the method and apparatus for sterilizing a liquid solution through radio-frequency according to the present invention, characterized by the appended claims below.

BRIEF DESCRIPTION OF THE DRAWINGS

This and other feature will become more apparent from the following description of a number of embodiments illustrated, merely as simplifying and non-limiting example, in the drawings of the attached figures.

DESCRIPTION OF THE INVENTION

Figure 1:
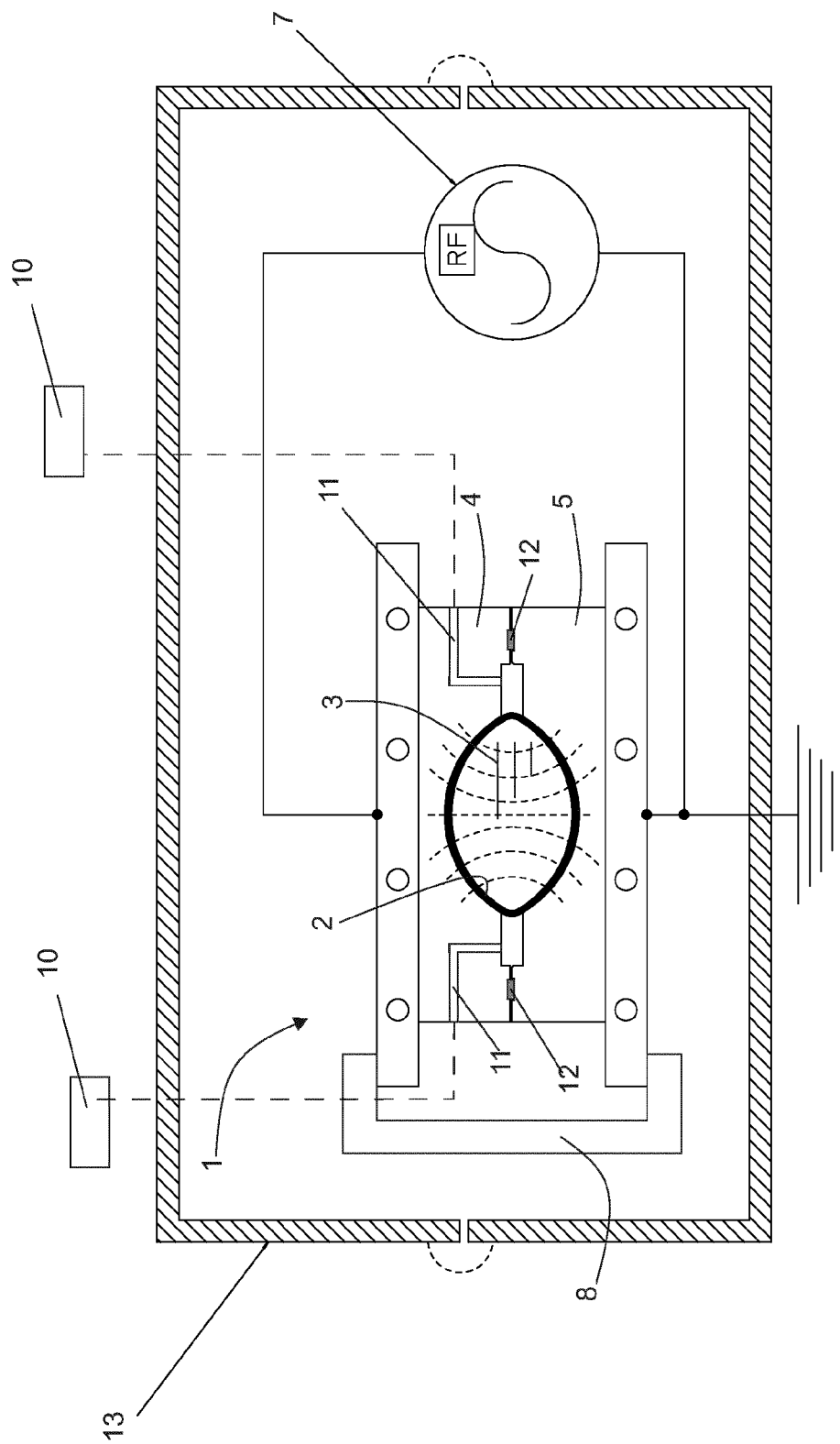
FIG. 1: shows the present sterilization system, along with the product to be sterilized.
Figure 2:
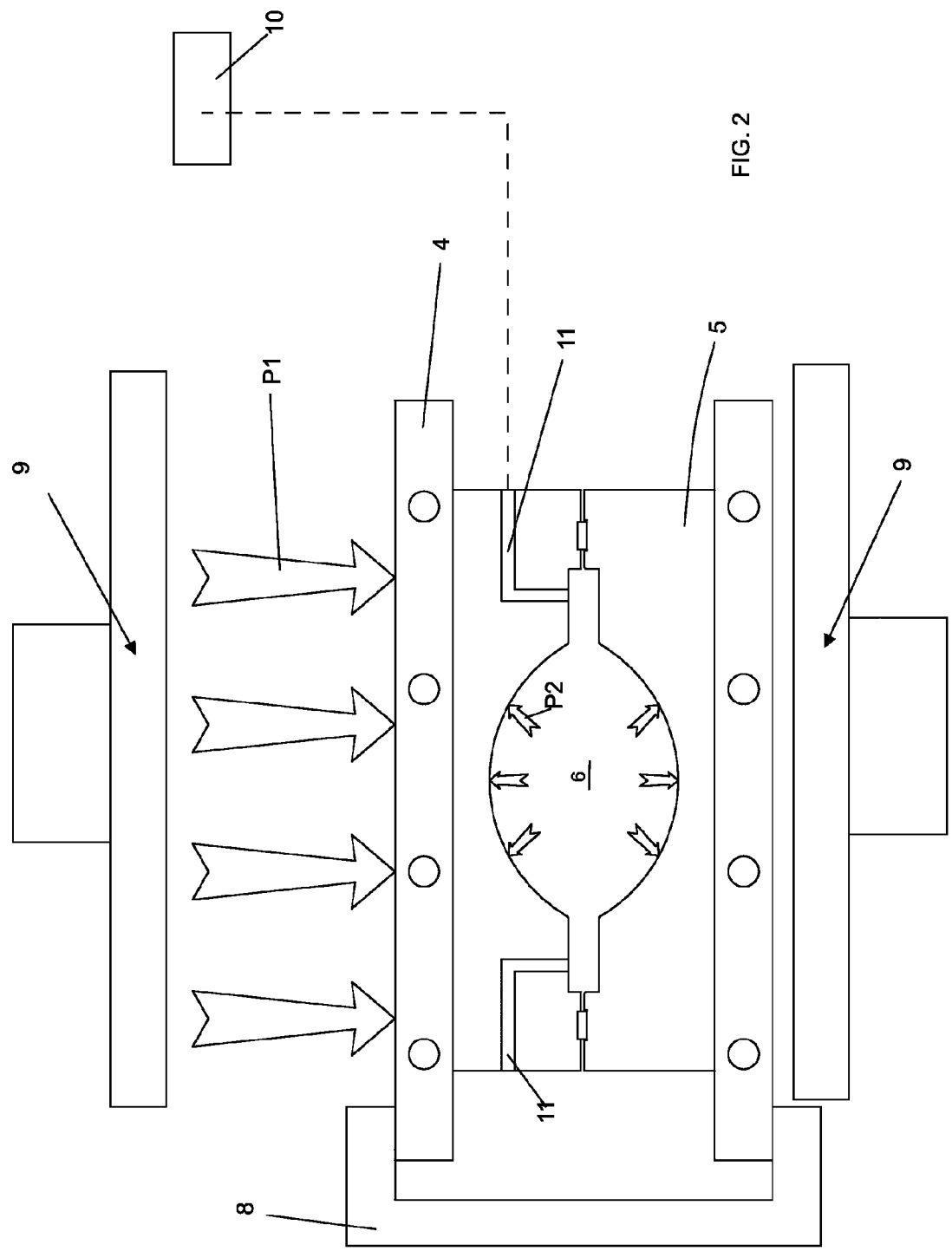
FIG. 2: shows again the present sterilization system, without the product therein.

Referring in particular to FIGS. 1 and 2, a system/apparatus for sterilizing containers 2 containing a non-demineralized or distilled liquid 3 therein, is indicated by 1. As for container 2, reference is made to glass containers or polymeric material bags containing medical solution.

System 1 comprises at least two half-shells 4 and 5, couplable to one another, with respective centrally shaped contact surfaces. If the half-shells are coupled, the electrode system so formed defines an internal cavity or chamber 6, suitably sized to receive the product to be treated, where the product means container 2 containing the solution to be sterilized.

System 1 is also equipped with a high-frequency generator 7 to create an electrical field across the two half-shells 4, 5 which act as an electrode and counter-electrode. Generator 7, further, includes a power control circuit, which is sized for a continuous service operation; preferably, the fundamental frequency is normally 27,12±0,6% MHz, that is a frequency allowed in electro-thermo-electrical applications on ISM equipment (Industrial, Scientific, Medical), nevertheless, also other frequencies allowed for ISM operation could be used without departing from the required scope of the invention.

Again, for generator 7, the active power output is selected based on the number of containers 2 being treated, also taking into account the amount of liquid solution being sterilized.

External means act on system 1 to secure half-shells 4 and 5 to each other, and in order to maintain the circuit electrically closed on the load, so as to make perfect contact between the electrode surface and container/s 2.

Figure 3:
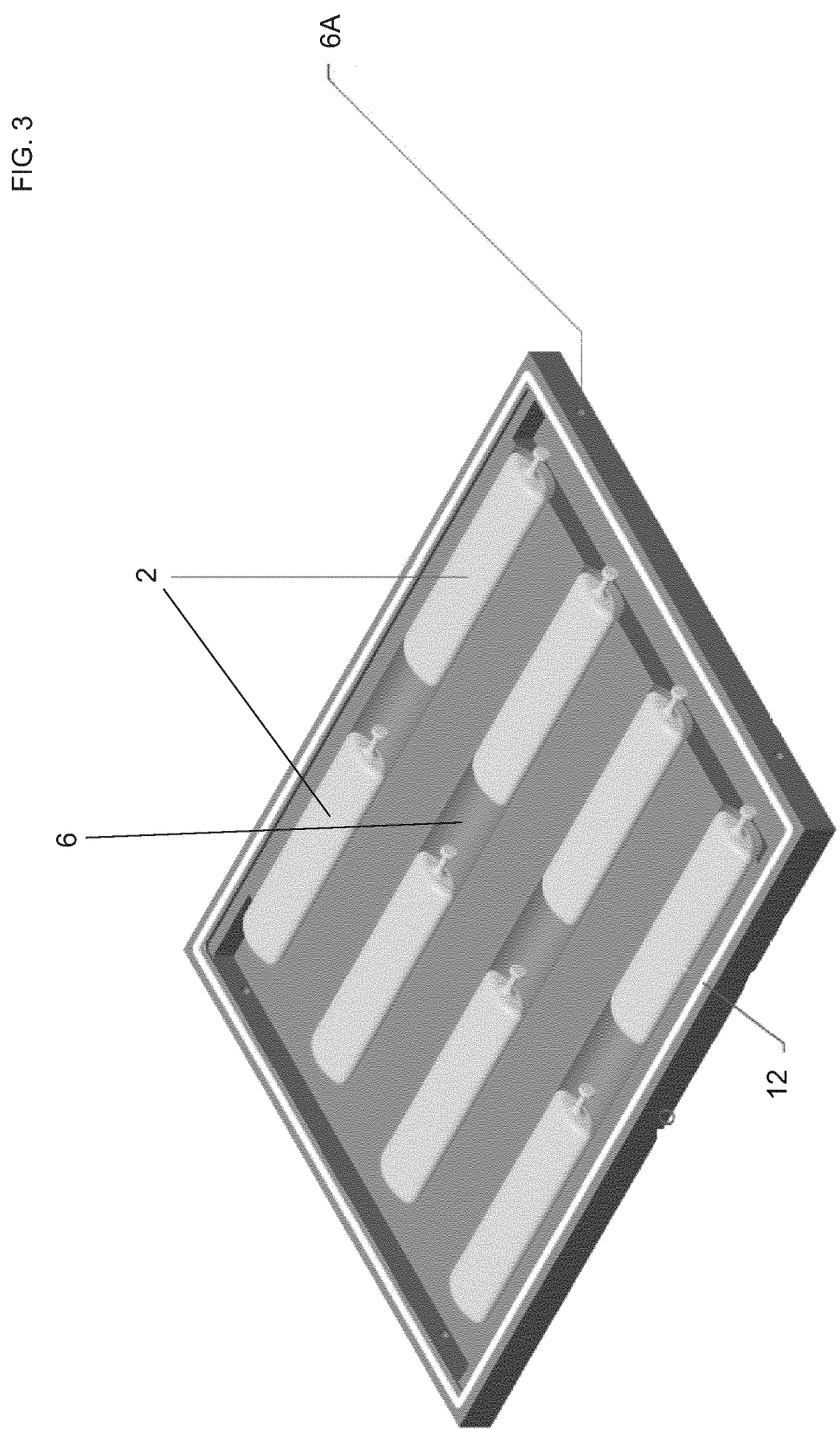
FIG. 3: shows lower half-shell in multiple load configuration of the products.

At least a compaction means, indicated by 9 in the figures, such a press, maintains a pressure P1 on half-shells 4 and 5, especially during the heating process, with the purpose of contrasting expansion of the bag and overcome a further counter-pressure P2 generated in internal chamber 6 by a pressurized gas generator 10, typically pressurized air, through at least a passage or duct 11 connectable through ordinary and well known union pipes. In FIG. 3, the inlet hole is denoted by 11A.

However, half-shells 4 and 5 may be held together by mechanical clamping means 8, acting in combination with press 9.

FIGS. 1 and 2 also show a perimetric gasket member 12 disposed on at least one of half shells 4 and/or 5, so that, once tightened to one another, half-shells:

Are kept galvanically isolated

Can withstand counter-pressure P2 within the so formed electrode system,.

Finally, numeral 13 indicates the shielding, outside system 1, for limiting the electromagnetic RF field irradiated by the system utilizing the generator RF frequencies.

Description of The Process

The sterilization process of a product as described above, and with the already illustrated system 1, comprises a heating step by supplying a capacitive high-frequency current, with electrodes, in a closed circuit electrode system, with a surface facing said product, followed by a cooling step by interruption of delivered current.

In addition, during at least past of said heating step, the system is provided with a counter-pressure P2 which acts within chamber 6 formed by half-shells 4 and 5.

Figure 4:
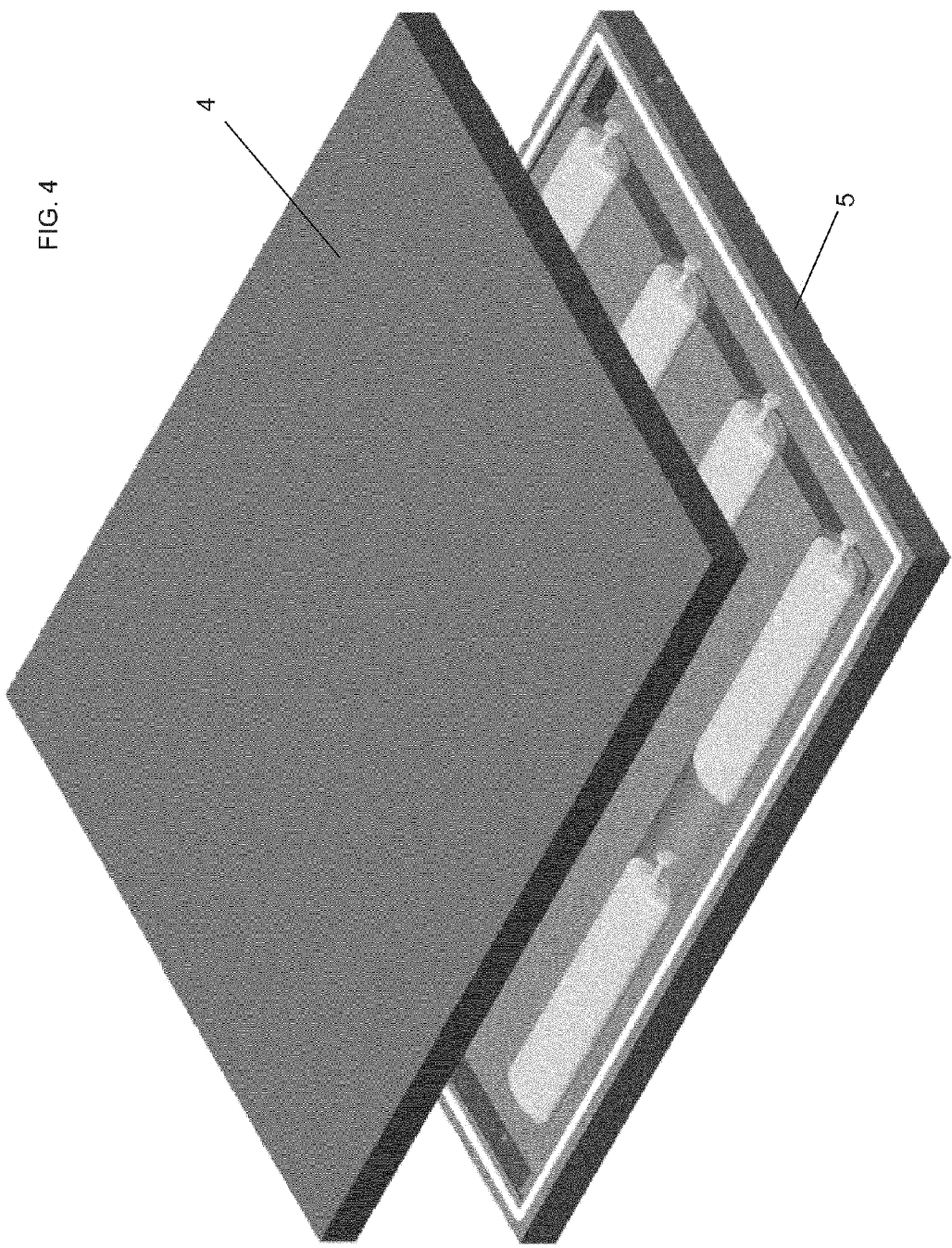
FIG. 4: still shows the multiple configuration, also with the upper half-shell.
Figure 5:
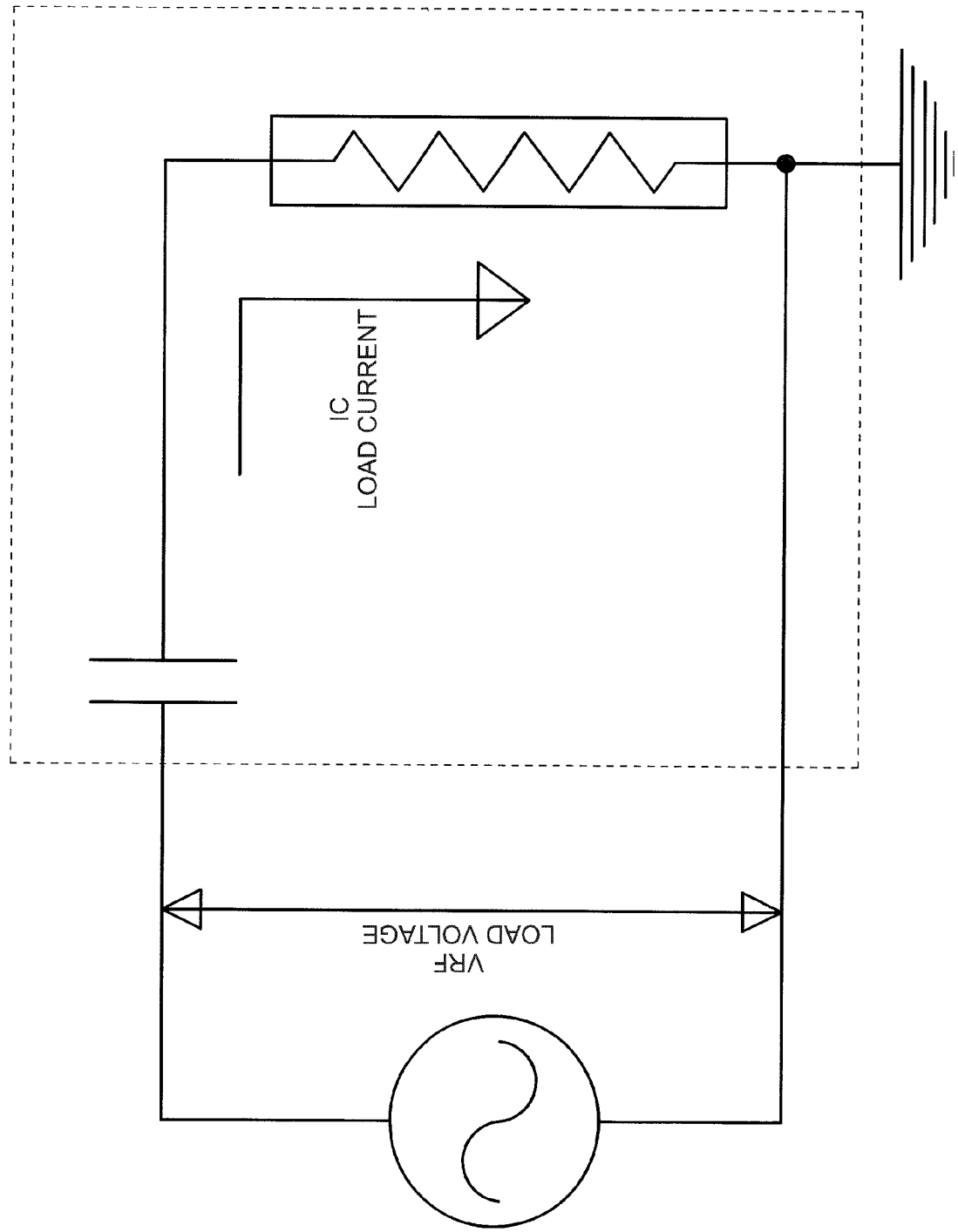
FIG. 5: shows the series equivalent RC circuit, as seen from the high-frequency generator.
Figure 6:
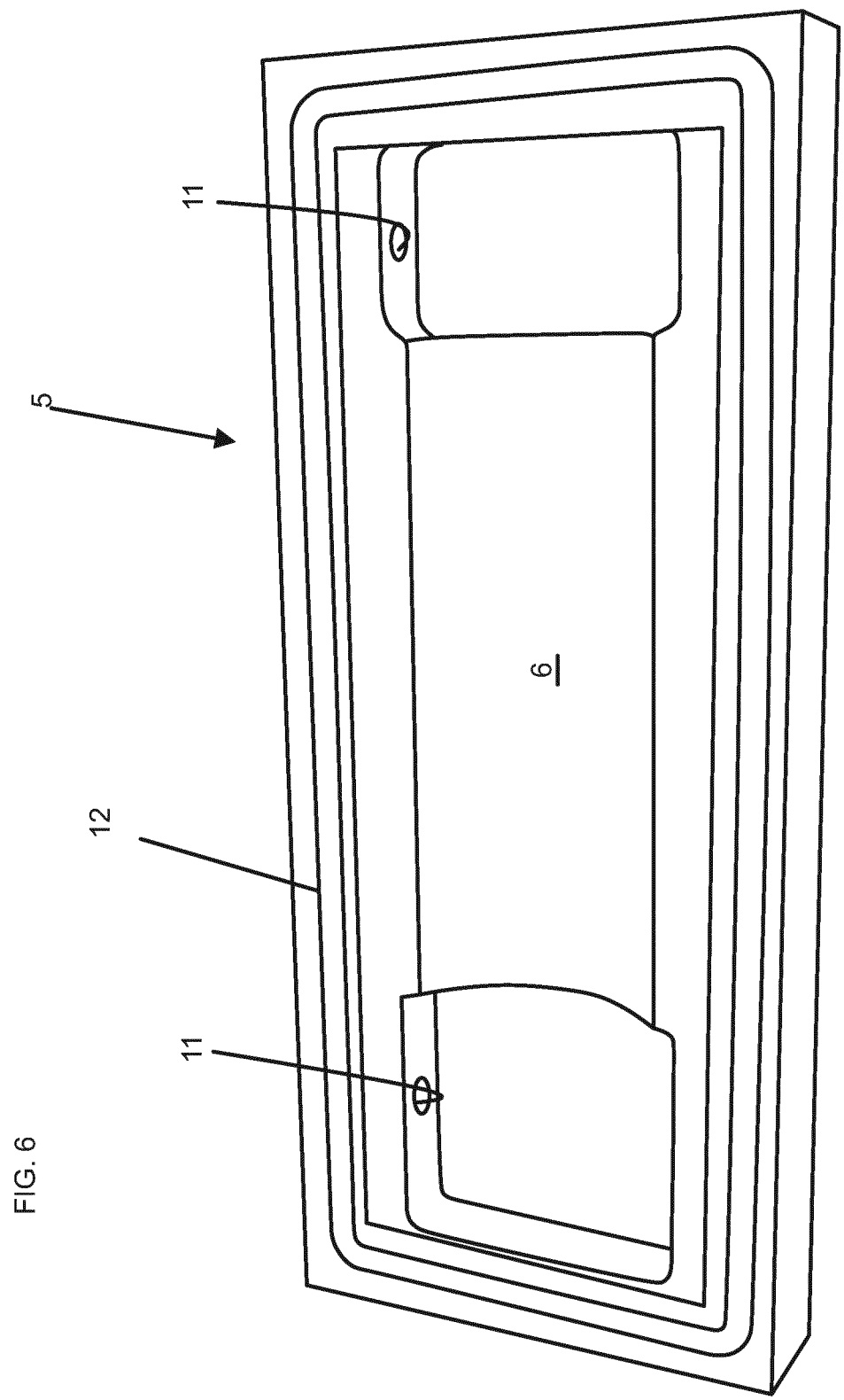
FIG. 6: shows lower half-shell with two duct holes for pressurization of the internal chamber.

In essence, during treatment, container 2 is in contact with the half-shell surfaces forming internal chamber 6, so that power is transferred to the solution to be sterilized by capacitive, low impedance, means, through the container itself; the solution is the conductive mass and heat is generated in the same solution due to direct flow of high-frequency current. FIG. 4 shows the equivalent RC circuit, seen from the generator; the utilized active power is proportional to the square of load tension Vrf and to the solution conductance 1/R, and therefore to the solution specific conductivity (milliSiemens/cm or microSiemens/cm), which, in turn, is strongly dependent on temperature and thus increasing during heating.

During the abovementioned steps, provision is made for generating two pressures:

First pressure is external to the electrode system, that is the half-shells, and provides for maintaining an external pressure that keeps them in a coupled relation, Second pressure is a counter-pressure acting from within the electrode system chamber, formed by two half-shells coupled and kept together; in such way, volumetric expansion of flexible containers is restricted in the head regions which are not in contact with the respective electrode, or sealing of rigid containers closure caps is secured. Such counter-pressure value ranges from 3 to 5 bars.

The abovementioned pressures P1, P2, in addition to the pressure of clamping means 8, will also be maintained during at least part of cooling of bag or container 2; only at a suitable operating temperature to avoid breaking the container and/or bag, the counter-pressure can be removed, thus releasing half-shells 4, 5.

In addition, the process provides minimization of the amount of waste power by establishing and controlling a strictly constant temperature liquid flow of the electrode and counter-electrode.

This is achieved by means of a cavity 14 on both electrodes 4 and 5, within which a hot fluid circulates, which is suitable for maintaining the system electrodes at a temperature between 35° C. and 60° C.

The amount of energy dissipated through the electrode surfaces is considerable: the described method provides minimization of such waste with constructional provisions such as to control and maintain the two electrodes temperature within a predetermined value (allowing for tolerances); this occurs as a result of liquid flow through the dedicated holes, in order to maintain strict control of the process significant parameters, power output from the high-frequency generator and sterilization temperature.

Active power output from the generator is chosen based on the number of bags or containers being treated, in addition to the quantity in liters of the solution being sterilized.

The invention claimed is:

1. A method of sterilizing a product constituted by a non-distilled or demineralized liquid solution contained in a rigid and/or flexible container, the method comprising:
   heating by capacitive supply of high-frequency current, from electrodes in a closed-circuit electrode system, wherein said electrodes face a surface of said product; and
   after the heating, cooling with interruption of the supplied current,
   wherein during at least part of said heating, a counter-pressure is supplied and acts inside the system and on the product being treated.

2. The method according to claim 1, wherein during at least part of said heating, the closed-circuit electrode system is maintained united by an external pressure.

3. The method according to claim 2, wherein during said heating, the container is maintained in contact with the surfaces of half-shells forming an internal chamber and the external pressure acts on heads of the container or on closure caps of the container.

4. The method according to claim 1, wherein said heating reaches at least a sterilization temperature.

5. The method according to claim 2, wherein said pressures are also maintained during at least part of said cooling.

6. The method according to claim 1, wherein an amount of dispersed energy is minimized, by controlling and fixing a strictly constant temperature for the liquid circulation of the electrode and a counter-electrode, the system electrodes being maintained at a temperature between 35° C. and 60° C.

7. An electrode system for actuating the method of sterilization of a product constituted by a non-distilled or demineralized liquid solution contained in a rigid and/or flexible container and according to claim 1, the electrode system comprising:
   two half-shells that are configured to be coupled together and closed on each other, shaped in a manner to define at least one internal chamber shaped to contain at least one container and a liquid solution of the container to be sterilized, said half-shells being respectively a power-supplied electrode and a counter-electrode at reference potential;
   a plurality of ducts, which enter inside the chamber through a respective inlet hole, from outside the system, said ducts being connected to at least one supply device configured to supply the counter-pressure pressure in the at least one internal chamber;
   at least one perimeter gasket on at least one of the two half-shells configured to maintain the two half-shells galvanically isolated and to oppose the counter-pressure pressure; and
   a high-frequency generator connected to said two half-shells.

8. The system according to claim 7, further comprising a compaction device configured to press on the two half-shells.

9. The system according to claim 7, further comprising a mechanical clamping device configured to shut the two half-shells.

10. The system according to claim 7, wherein said two half-shells comprise a plurality of cavities configured to allow the passage of a fluid.

* * * * *